(12) United States Patent
Aboufares (10) Patent No.: US 11,471,071 B2
(45) Date of Patent: Oct. 18, 2022

(54) METHOD AND APPARATUS FOR MEASURING THE LENGTH OF A VASCULAR ANATOMIC LESION

(71) Applicant: Ali Aboufares, New York, NY (US)

(72) Inventor: Ali Aboufares, New York, NY (US)

(*) Notice: Subject to any disclaimer, the term of this patent is extended or adjusted under 35 U.S.C. 154(b) by 0 days.

(21) Appl. No.: 15/790,752

(22) Filed: Oct. 23, 2017

(65) Prior Publication Data

US 2019/0117120 A1    Apr. 25, 2019

(51) Int. Cl.
| | | |
|---|---|---|
| *A61B 5/107* | (2006.01) | |
| *A61M 25/00* | (2006.01) | |
| *A61B 5/00* | (2006.01) | |

(52) U.S. Cl.
CPC .......... *A61B 5/1076* (2013.01); *A61B 5/1072* (2013.01); *A61B 5/6852* (2013.01); *A61M 25/0026* (2013.01); *A61M 2025/0008* (2013.01)

(58) Field of Classification Search
CPC . A61B 5/1076; A61B 5/6852; A61B 5/02014; A61B 5/1072; A61M 25/0026; A61M 25/09; A61M 2025/0008
See application file for complete search history.

(56) References Cited

U.S. PATENT DOCUMENTS

| | | | | |
|---|---|---|---|---|
| 6,078,832 | A * | 6/2000 | Lenker | A61M 25/00 600/585 |
| 6,575,932 | B1 * | 6/2003 | O'Brien | A61M 25/007 604/101.01 |
| 6,613,002 | B1 * | 9/2003 | Clark | A61B 5/1076 600/104 |
| 8,206,370 | B2 * | 6/2012 | Von Oepen | A61M 25/0029 604/164.01 |
| 2015/0119702 | A1 * | 4/2015 | Mulumudi | A61B 5/065 600/424 |

* cited by examiner

*Primary Examiner* — Carrie R Dorna (57) ABSTRACT

A dual lumen catheter with a measuring scale is disclosed. The catheter has a pair of lumens, one of which is adapted to receive a measuring scale for measuring the length of a lesion within the body. A view port is provided to allow the user to view the measuring scale and determine the length of the lesion.

13 Claims, 9 Drawing Sheets

Pull-back distance and
therefore, lesion length measurement

METHOD AND APPARATUS FOR MEASURING THE LENGTH OF A VASCULAR ANATOMIC LESION

CROSS-REFERENCE TO RELATED APPLICATION

This application claims priority to application No. 62/412,007 filed on Oct. 24, 2016 and entitled "Method And Apparatus For Measuring The Length Of A Vascular Anatomic Lesion."

TECHNICAL FIELD

The present invention generally relates to the field of medical devices and more particularly, is directed to a method and apparatus for measuring the length of a vascular anatomic lesion.

BACKGROUND

Medical devices for diagnosis and treatment play an important role in the effective and efficient delivery of healthcare services. Many of the advancements in healthcare have come as a result of improvements in such devices.

One example of the need for effective medical devices is the care and treatment of the cardiovascular system in the human body. While each of the major systems in the body plays key roles in maintaining proper body function, the cardiovascular system is of particular importance. The cardiovascular system is responsible for circulating blood throughout the body via the heart, arteries and veins, delivering oxygen and nutrients to organs and cells, especially the brain, and carrying their waste products away. More than any other system, the body will not tolerate a malfunctioning cardiovascular system for very long.

Many of the ailments that affect the cardiovascular system require a surgical intervention. For example, a catheter containing medications or miniature instruments is often inserted into a blood vessel for treatment and/or analysis of lesions or other damaged tissue. In such cases, accurate measurements of anatomic lesion length are of paramount importance.

This is particularly essential when device therapy, or endoprosthesis, is utilized to insert, e.g., stents or endografts. Prior to implanting a stent to treat a specific vascular lesion in its entirety, the healthcare provider estimates the length of the segment to be treated based on visual approximations. Occasionally, the length of the lesion is under-estimated, leading to the treatment zone being less than required to treat the entire ailment. Such a condition is known in the art as a "geographical miss" and is associated with unfavorable post-procedural angiographic and clinical outcomes. The use of additional stents, and the associated surgical and intervention risks, are often the only solution to a geographical miss.

Thus, there is a great need in the art for a measuring device that will reduce the likelihood of geographical misses by accurately measuring the length of a lesion. Such a device will minimize the need for additional stents and the associated medical risks and complications.

BRIEF DESCRIPTION OF THE DRAWINGS

The novel features of the present invention are set out with particularity in the appended claims, but the invention will be understood more fully and clearly from the following detailed description of the invention as set forth in the accompanying drawings in which:

DESCRIPTION OF THE PREFERRED EMBODIMENT

A preferred embodiment of the present invention will be described with reference to the figures.

The present invention is a dual lumen plastic catheter intended for use in, for example, the coronary and/or the peripheral vasculature. Other uses and applications include the genitourinary system (e.g., ureter and pulmonary stents and like). The catheter houses two lumens in parallel for a short distance then continues as a single lumen proximally to the outside of the body.

The first lumen is a rapid exchange (RX) delivery lumen and is designed to accommodate a 0.014 inch (0.36 mm) guidewire which allows the catheter to be advanced from outside the human body to the specific blood vessel. The first lumen may also be sized to accommodate other guidewire sizes that are known in the art, such as 0.018 inch and 0.035 inch guidewires. The second lumen is an over-the-wire (OTW) that accommodates a 0.023 inch (0.58 mm) wire, or "ruler". The second lumen is longer that the first lumen and extends to become the catheter itself.

A "marker" is placed at distal end of the lesion. The "marker" is a radio-opaque band that represents a fusion point on the catheter tip. The fusion point is the overlap of the radiopaque catheter distal tip and the inner ruler distal tip. In accordance with the present invention, this is considered the baseline state.

To measure a lesion length, the operator pulls back the "ruler" within the catheter while observing the partial marker move proximally under continuous X-ray fluoroscopy. Once the desired lesion length/distance is achieved, the operator records the distance displaced on the ruler (from the outside) at the hub using a graduated millimeter marking millimeter (or inch) marking printed on the ruler along its length.

Such a system allows the exact measurement of the lesion as the distance measured after the pull-back is the anatomic lesion length.

Figure 1:
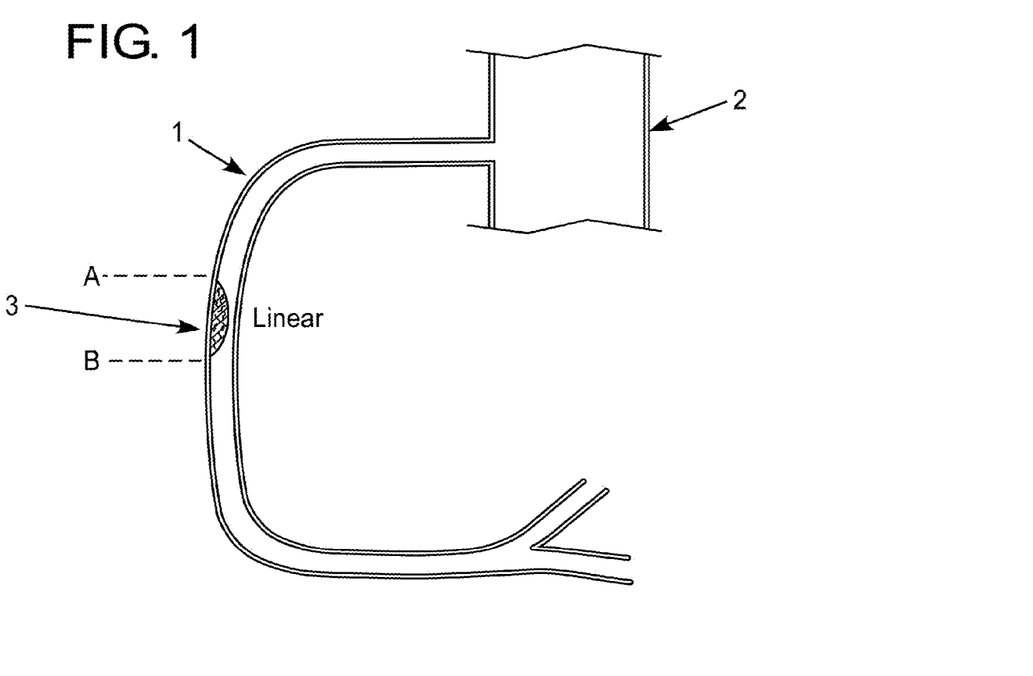
FIG. 1 illustrates a lesion formed in a straight, or linear, portion of a blood vessel.

FIG. 1 illustrates a representative coronary artery 1 take-off from an aorta 2. A lipid plaque, or lesion 3 is shown in a mid-segment of artery 1. Typically, lesion length is defined by the distance between points A and B, as shown in FIG. 1. In FIG. 1, lesion 3 is in an area of artery 1 that is essentially straight or linear.

In order to treat lesion 3, the operator dilates the blood vessel at that location using a balloon/stent equal to or a bit longer than the distance A-B. The classic teaching is to treat normal-to-normal vessel thus extending a few millimeters on each end of A and B.

Figure 2:
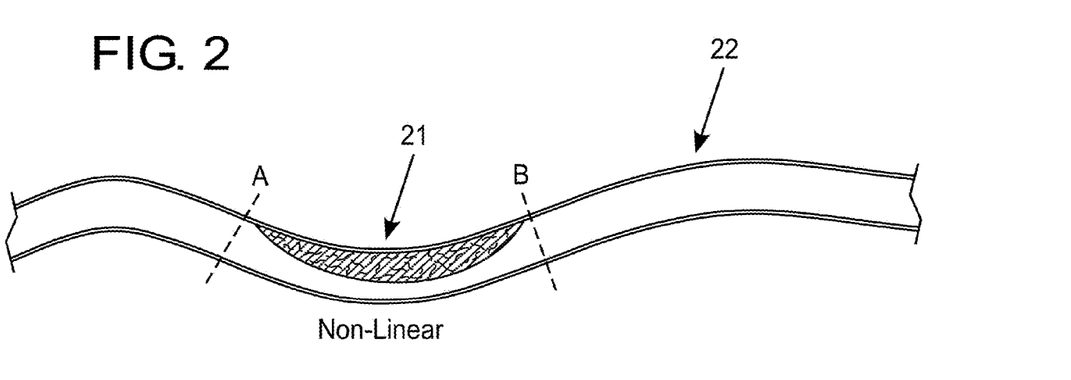
FIG. 2 illustrates a lesion formed in a curved, or non-linear, portion of a blood vessel.

FIG. 2 illustrates a lesion 21 that is in an area of vessel 22 that is not straight on, in other words, non-linear. In actuality, the length A-B of lesion 21 may be the same as lesion 3 shown in FIG. 1. However, the non-linearity of vessel 22 in the area of lesion 21 leads to errors in visual estimates of its length as inferred from a 2-D image of a 3-D structure.

Figure 3:
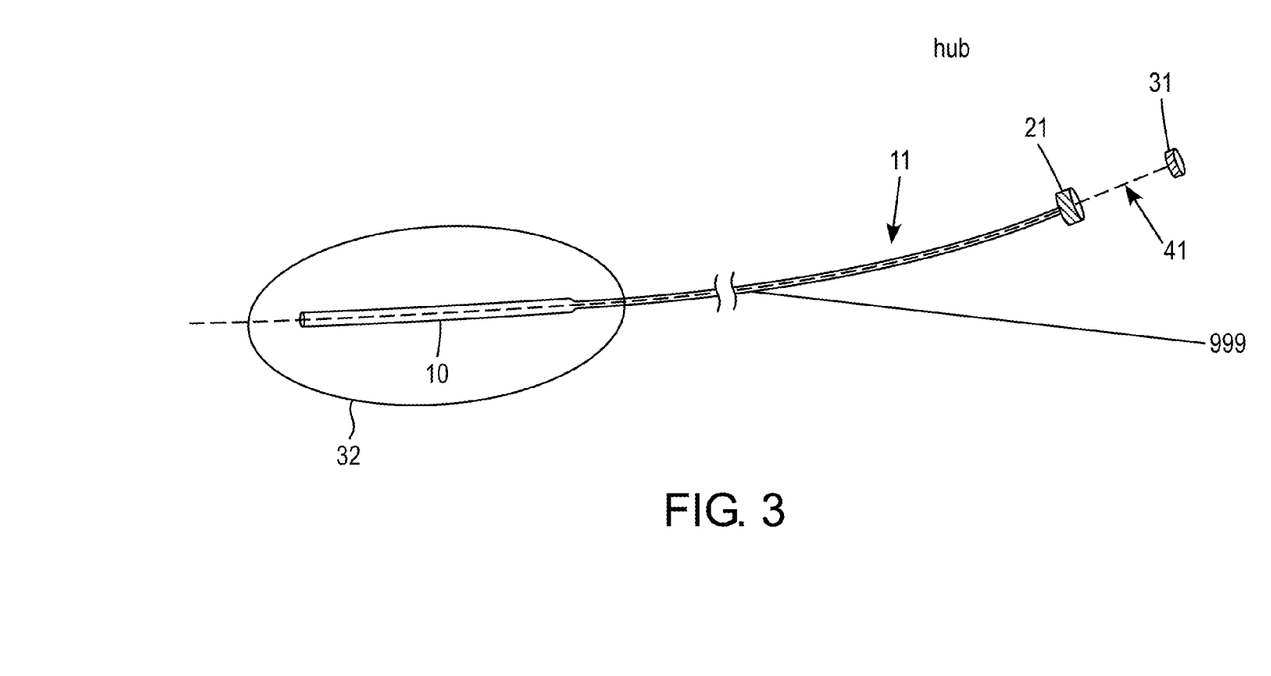
FIG. 3 is an elevation view of one embodiment of a device for measuring the length of lesions in accordance with the present invention.

FIG. 3 illustrates of the lesion length measuring tool (LLT) of the present invention. The proximally end 31 is shown in greater detail in FIG. 4 and the distal end 32 is shown in greater detail in FIG. 5.

With further reference to FIG. 3, a regular guidewire 999 of variable diameter ranging between 0.014 inch to 0.035 inch is introduced in a hollow vascular structure in the usual manner.

Over guidewire 999, and in a monorail fashion, a catheter 10 is introduced and placed at the target lesion to be studied. Catheter 10 has proximal hub 21 that is an extension of catheter 10. Hub 21 is a female/receiving bolt, or similar fastening device, that accommodates another smaller diameter catheter 41 in its center. At the proximal end of inner catheter 41, a male screw 31 is provided that can fit tightly into hub 21.

Figure 4A:
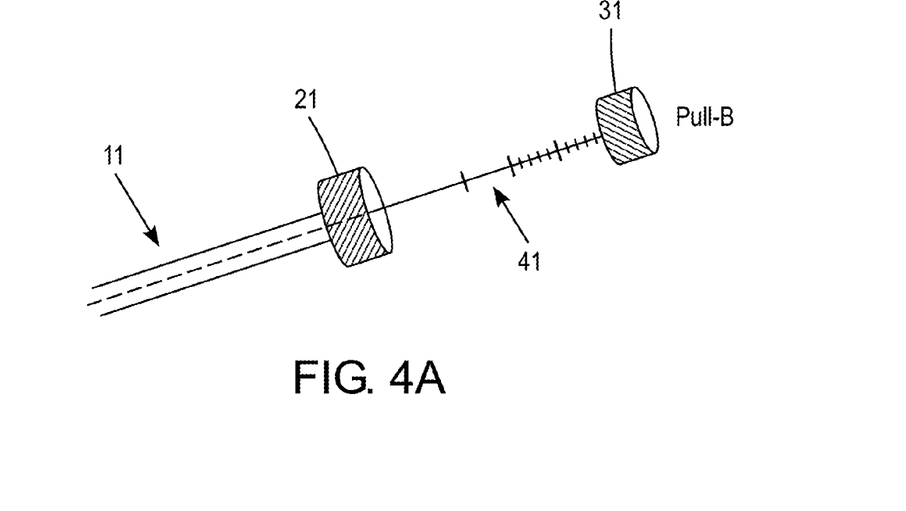
FIGS. 4A-4B illustrate the marking measurement used to determine the length of a lesion in the embodiment of FIG. 3.
Figure 4B:
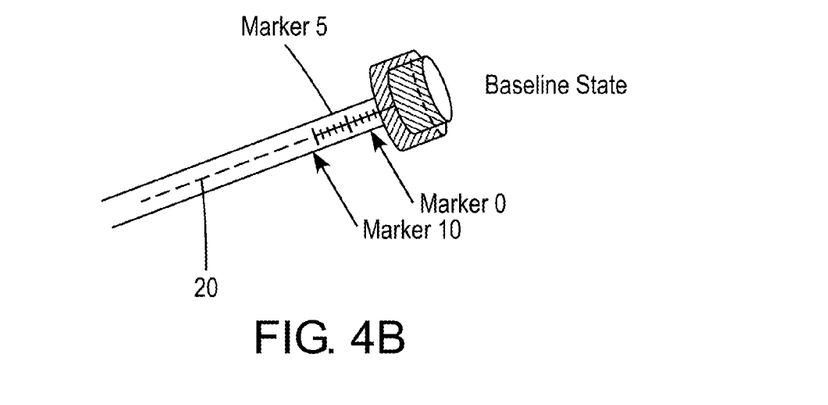

FIG. 4 represents the relationship between the catheters in two different states. Catheter 11 represents one of the lumens that constitute catheter 10. Catheter 11 has a closed tip on its distal end. In the "baseline state" as shown in FIG. 4-B, catheter 41 is screwed all the way in with the hubs 21-31 in full contact.

In the "pull-back" state as shown in FIG. 4-A, which represents the unscrewing of male screw 31 from hub 21, catheter 41 when exposed has millimeter marks engraved on it similar to a measuring ruler. The zero mark is at the hub 31 and the ruler runs in an ascending numbers fashion distally into catheter 11. In another embodiment, the reference marks run in a descending order. Whether the reference marks are ascending or descending, it is important that they be consistently spaced so that they can be used to indicate distance.

Figure 5:
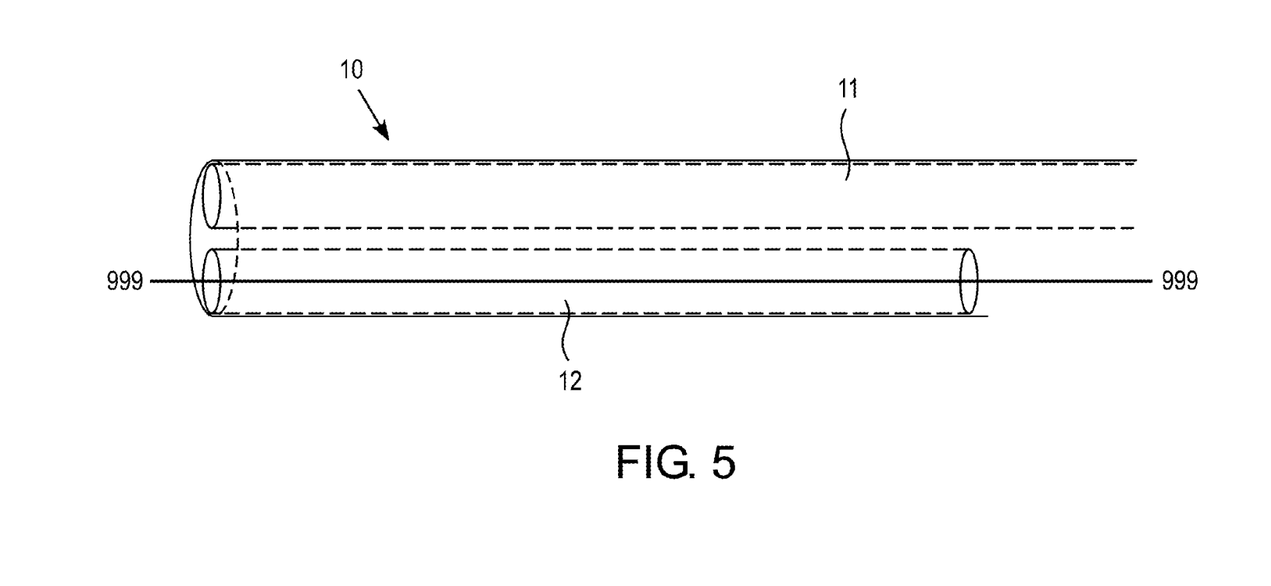
FIGS. 5-7 illustrate the construction of a device for measuring the length of a lesion in accordance with the present invention.

FIG. 5 is a detailed view of the distal end of catheter 10. As described above, catheter 10 is comprised of two lumens 11 and 12 of variable diameters. Lumen 12 is a short lumen that extends typically 10-20 cm in length starting distally. Lumen 12 also accommodates guidewire 999 which is the initial instrument introduced in the vessel.

Lumen 11 accommodates catheter 41, which is the "ruler" in accordance with the present invention.

Figure 6:
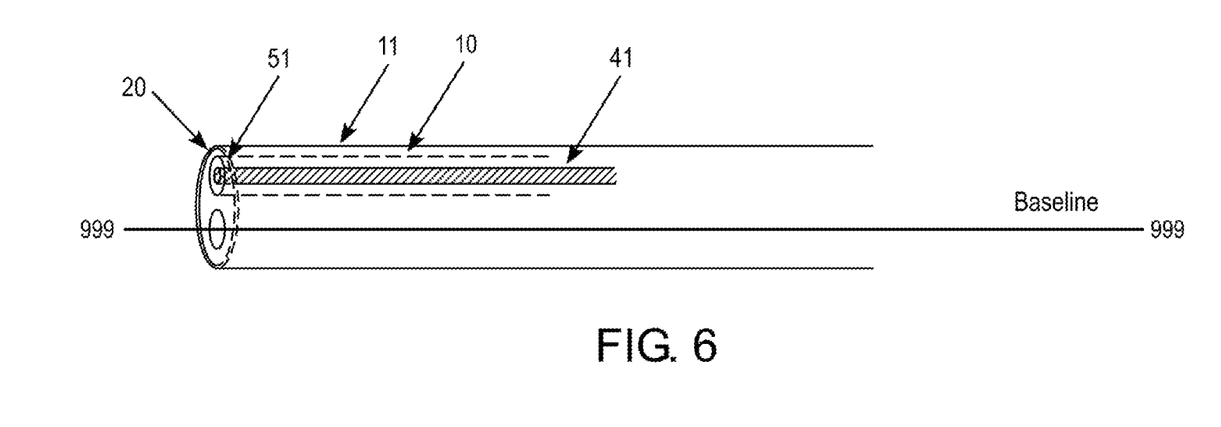

FIG. 6 illustrates the "baseline" state. In this state, catheter 41 inside lumen 11 is advanced all the way in (distally) such that the tip of catheter 41 is at the tip of catheter 10. This position represents a fusion point at the tip of catheter 10 which also serves as a radiopaque marker. This marker 51 is comprised of the tip of catheter 41 and the tip of catheter 10 and has a circumferential radiopaque band 20. Catheter 41 is radiopaque along its length.

Figure 7:
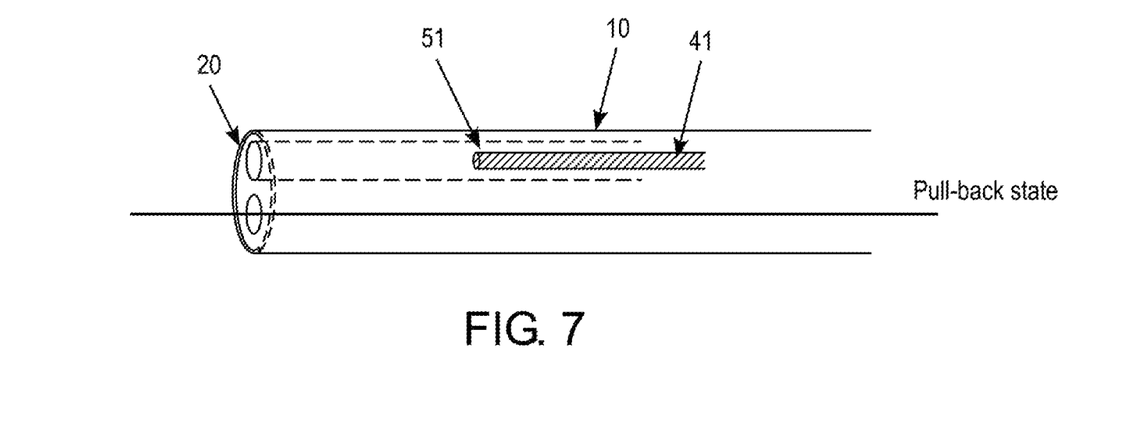

FIG. 7 illustrates the "pull-back" state. When hubs 21-31 are disunited and catheter 41 is pulled out by pulling out on hub 31, there is a coaxial displacement of catheter 41 proximally. This results in the ability to visualize two distinct radiopaque points namely the radiopaque tip 20 and the inner ruler tip 51. The distance between the two points is the pull-back or lesion length measurement distance.

Figure 8:
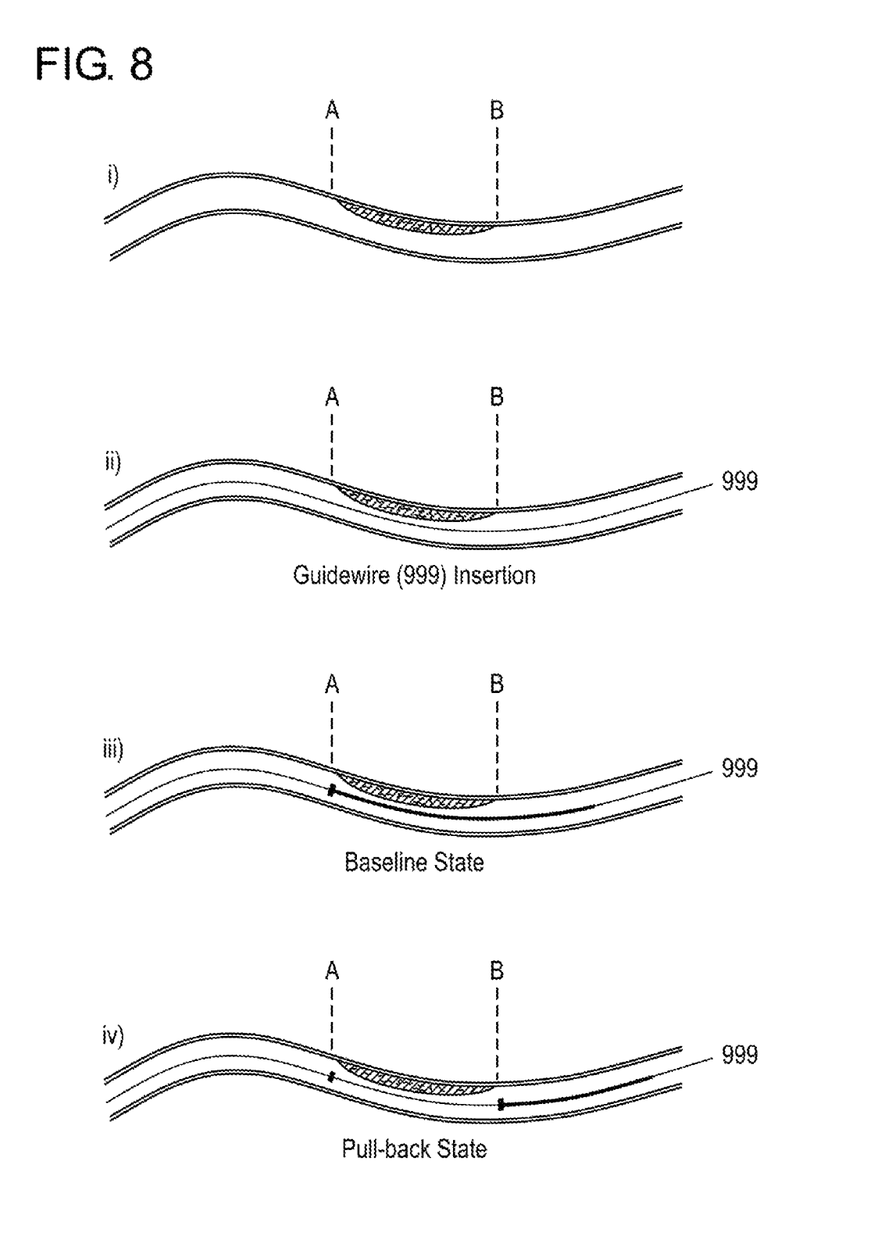
FIG. 8 illustrates the progression of use of the measuring device of the present invention.

FIG. 8 illustrates the operation of the device of the present invention as follows:
i) Tortuous coronary artery with a lesion with an anatomic length of A-B;
ii) Guidewire 999 is inserted in the vessel;
iii) Baseline state where the system in its entirety is introduced and the catheter 10 tip is placed at the distal part of the lesion A; and
iv) Pull-back follows by withdrawing catheter 41 proximally until the desired fluoroscopic point is reached, in this case point B which represents the proximal end of the lesion. As demonstrated, the radiopaque markers provide guidance on the location of the catheter(s) in relation to lesion.

Figure 9:
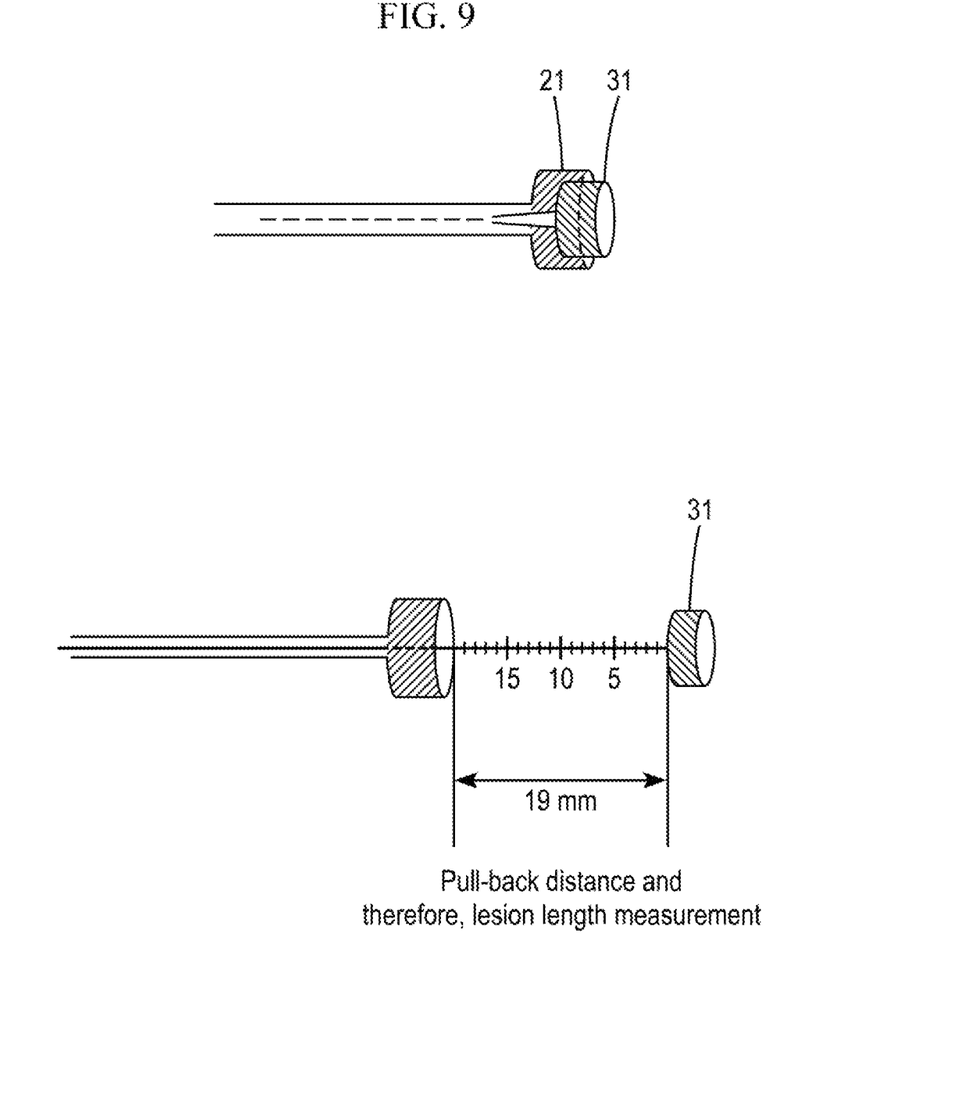
FIG. 9 illustrates in more detail the measurement marking scale of the measuring device of the present invention.

With reference to FIG. 9, note that when pull-back occurs as described above, the distance created by withdrawing catheter 41 coaxially proximally with a resultant distance between tip 20 and tip 51. This is exactly equal to the distance traveled on the ruler (catheter 41) between hub 21-31. In this case the pullback distance disclosed measures 19 mm as seen from the external parts of the lesion length measuring tool of the present invention.

As noted above with respect to FIG. 9, the distance created by withdrawing catheter 41 results in a corresponding distance between tips 20 and 51. This distance is exactly equal to the distance traveled on the ruler (catheter 41) between hubs 21-31 as shown in FIG. 9.

Figure 10A:
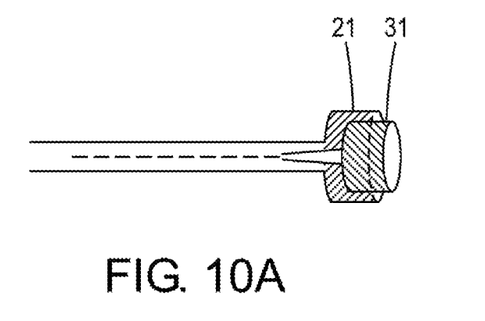
FIGS. 10A-10B and 11 illustrate a computer control system for the measuring device of the present invention.
Figure 10B:
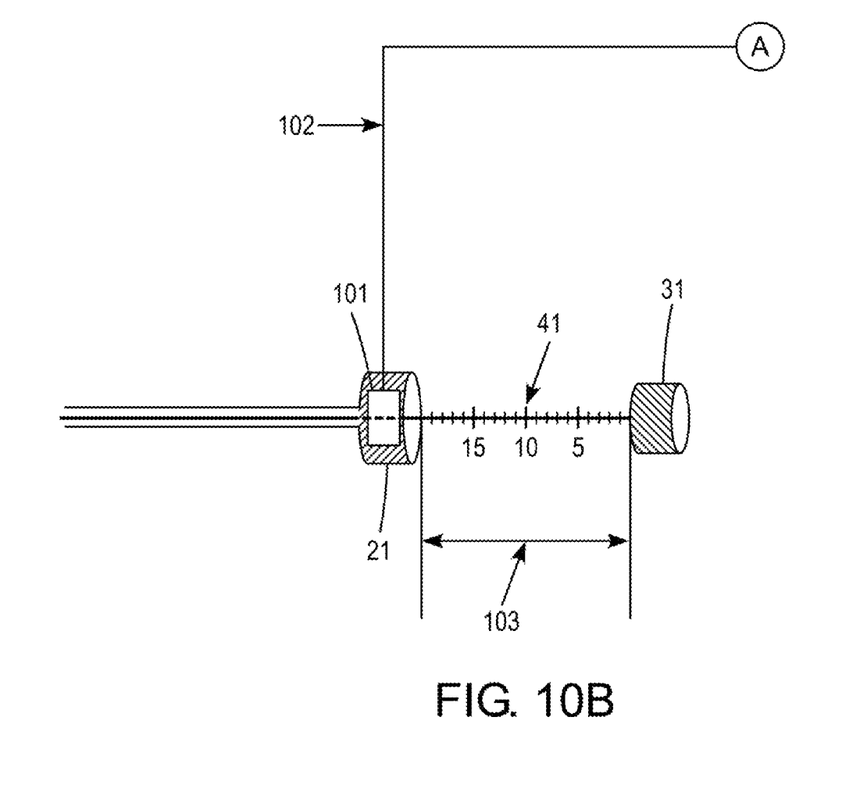

FIG. 10 illustrates a further embodiment of the present invention. In this embodiment, a measuring sensor 101 is provided within hub 21. When hub 31 is adjacent to hub 21, indicating that catheter 41 has not been withdrawn to any degree, measuring sensor 101 returns an electrical signal 102 indicating that distance 103 is 0.

When hub 31 is fully extended away from hub 21, and distance 103 is at its maximum, measuring sensor 101 returns an electrical signal indicating the maximum travel of catheter 41. For those intermediate distances between 0 and the maximum travel of catheter 41, measuring sensor 101 returns real time signals corresponding to distance 103 at all points in time.

Figure 11:
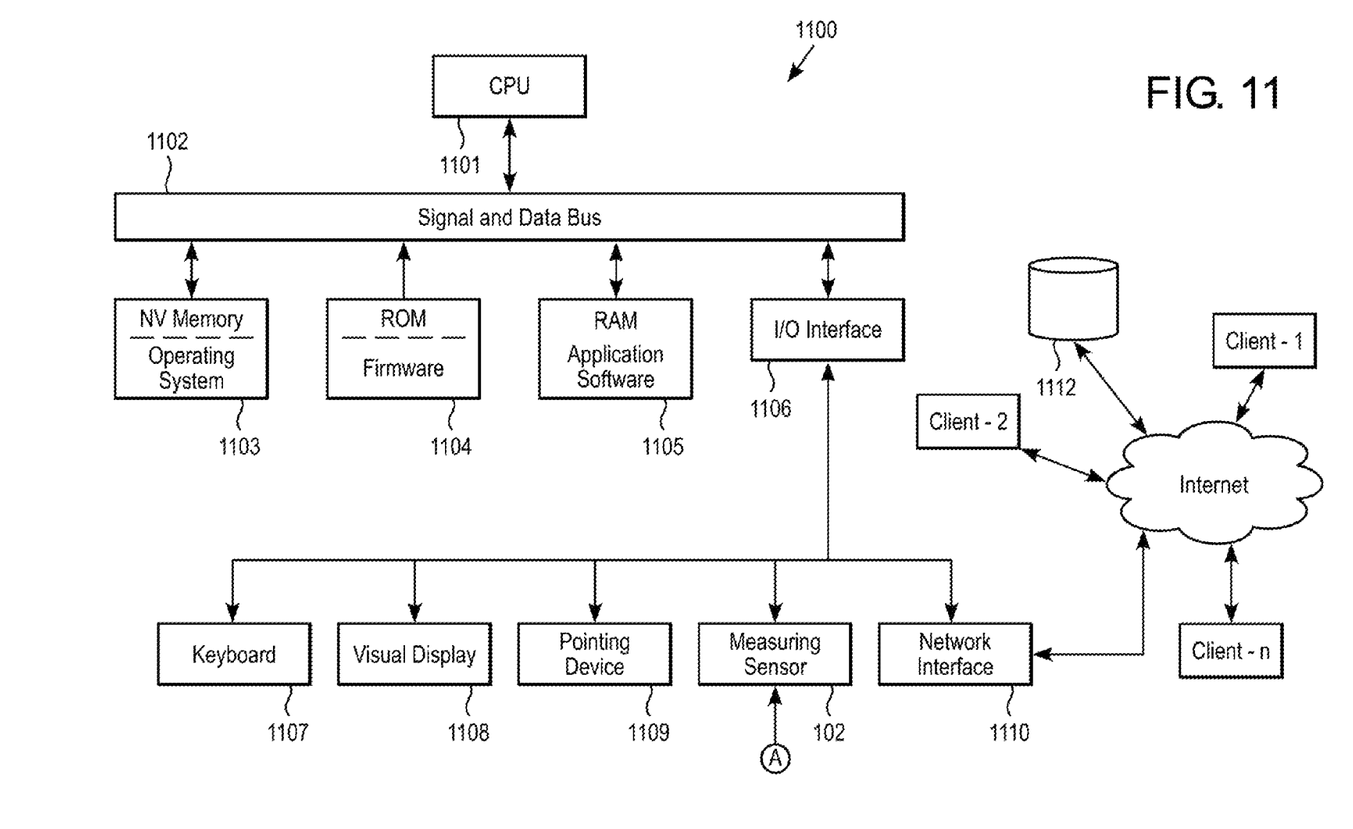

Electrical signal 102 is provided to Control Unit 1100 illustrated in FIG. 11.

Control Unit 1100 includes a CPU 1101. The CPU is used for executing computer software instructions as is known in the art. CPU 1101 is coupled to a number of other elements via a signal and data bus 1102 as is also known in the art. These elements include ROM (Read Only Memory) 1104 which may be used to store computer software instructions, RAM 1105 (Random Access Memory) which also may be used to store computer software instructions, I/O Interface 1106 which may be used to interface CPU 1101 to elements and/or functions that are external to CPU 1101, and Non Volatile Memory 1103 which may be used to store computer software instructions as well.

As mentioned above, I/O Interface 1106 is used to interface CPU 1101 to elements or functions that are external to the CPU. These external elements might include Keyboard 1107, Visual Display 1108, Pointing Device 1109, such as a mouse or touch pad, and Network Interface 1110.

Depending on the tasks to be performed by CPU 1101, its computer software instructions might be divided into two or more separate and distinct categories which are stored in separate portions of ROM 1104, RAM 1105 and/or Non Volatile Memory 1103. In some devices, a basis set of low level operating instructions, known in the art as firmware, might be stored in, for example, ROM 1104. These low level rudimentary instructions provide the necessary instructions for how the controller communicates with the other computer hardware. Such instructions are necessary for the controller to perform any useful work, regardless of the application for which the device is to be used.

The computer instruction set that is executed by CPU 1101 to perform the particular tasks required of Control Unit 1100 is often called "application software" and operationally "sits" on top of the firmware.

As illustrated in FIG. 11, the application software is stored in RAM 1105. The application software could also be stored in ROM 1104 or in Non Volatile Memory 1103.

Network interface 1110 allows Control Unit 1100 to be connected to the Internet, or to other networks, such as local area or wide area networks. Such a network connections allows client computers Client-1 to Client-n to connect the Control Unit 1100.

As further shown in FIG. 11, measuring signal 102 is coupled to Control Unit 1100. In accordance with the present invention, application software 1105 is programed to received and displayed a visual image on Visual Display 1108 which indicates the precise distance that catheter 41 has traveled and its location. Visual Display 1108 can be implemented in the form of a conveniently placed computer monitor that will give the surgeon a much easier to view indication of the location of the catheter at any point in time.

Network Interface 1110 allows client computers to observe and monitor the procedure remotely.

While the foregoing specification teaches the principles of the present invention, with examples provided for the purpose of illustration, it will be appreciated by one skilled in the art from reading this disclosure that various changes in form and detail can be made without departing from the true scope of the invention.

I claim:

1. A dual lumen catheter with a measuring scale, said dual lumen catheter comprising:
   a first lumen adapted to receive a guidewire,
   a second lumen adapted to receive said measuring scale in sliding engagement with said second lumen, wherein said first lumen and said second lumen are positioned in parallel for a first distance and thereafter said second lumen proceeds for a further distance as a catheter; and
   wherein when said dual lumen catheter is adapted for insertion into a human body, said measuring scale having a first marker indicating the distal end of a lesion when said measuring scale is moved to a first position within said second lumen and a second marker indicating the proximal end of said lesion when said measuring scale is moved to a second position within said second lumen; and
   wherein the distance between said first and second markers indicates the length of said lesion.

2. The dual lumen catheter of claim 1, wherein said first lumen is a rapid exchange delivery lumen.

3. The dual lumen catheter of claim 1, wherein said second lumen is an over-the-wire lumen.

4. The dual lumen catheter of claim 1, wherein said first and second markers are part of a plurality of markers along said measuring scale, the distance between said plurality of markers indicating a predetermined distance of a lesion.

5. The dual lumen catheter of claim 1, wherein said first and second lumens are formed of a plastic material.

6. The dual lumen catheter of claim 5, wherein said plastic material is radiopaque.

7. The dual lumen catheter of claim 5, wherein said plastic material is opaque.

8. The dual lumen catheter of claim 1, wherein said first lumen is adapted to accommodate guidewires in the range of 0.014 inches to 0.038 inches.

9. The dual lumen catheter of claim 1, wherein said catheter has a baseline state and a pull-back state, wherein said catheter has a plurality of graduation marks representing a linear scale that are visible to the user when said catheter is in said pull-back state.

10. The dual lumen catheter of claim 1, wherein at least a portion of said catheter is made of a radiopaque polymer material.

11. A system for measuring the length of a pre-marked structure of interest, said system comprising:
    a delivery catheter;
    an elongated measuring scale having an in vivo portion at one end and an in vitro portion at the other end, said in vitro portion having a plurality of measurement graduation marks and a hand grasp;
    a first lumen within said delivery catheter and being adapted to receive a guidewire;
    a second lumen within said delivery catheter and being adapted to receive said measuring scale in sliding engagement with said second lumen, wherein said first lumen and said second lumen are positioned within said delivery catheter in parallel for a first distance and thereafter said second lumen proceeds for a further distance within said catheter;
    wherein when said system is inserted into a human body, the end of said in vivo portion of said measuring scale is moved to a first marker indicating the distal end of said pre-marked structure to be measured and then moved to a second marker indicating the proximal end of said structure to be measured; and
    wherein the relative movement of said measuring scale between said first and second markers indicates the length of the structure to be measured.

12. The system of claim 11, wherein said first lumen is a rapid exchange delivery lumen.

13. The system of claim 11, wherein said second lumen is an over-the-wire lumen.

* * * * *